(12) United States Patent
Marek et al.

(10) Patent No.: US 7,607,335 B2
(45) Date of Patent: Oct. 27, 2009

(54) PARTICULATE SAMPLER SYSTEM FLOW CALIBRATION

(75) Inventors: Gerald Marek, Ann Arbor, MI (US); Shahin Sabokdast Nudehi, East Lansing, MI (US)

(73) Assignee: AVL North America Inc., Plymouth, MI (US)

( * ) Notice: Subject to any disclaimer, the term of this patent is extended or adjusted under 35 U.S.C. 154(b) by 776 days.

(21) Appl. No.: 11/386,911

(22) Filed: Mar. 22, 2006

(65) Prior Publication Data

US 2006/0216826 A1 Sep. 28, 2006

Related U.S. Application Data

(60) Provisional application No. 60/664,277, filed on Mar. 22, 2005.

(51) Int. Cl.
G01P 21/00 (2006.01)
G01F 25/00 (2006.01)
G01N 21/00 (2006.01)
G01N 27/00 (2006.01)
G01N 31/00 (2006.01)

(52) U.S. Cl. .......................... 73/1.35; 73/1.34; 73/1.07; 73/1.06

(58) Field of Classification Search .................. 73/1.35, 73/1.34, 1.07, 1.06
See application file for complete search history.

(56) References Cited

U.S. PATENT DOCUMENTS 6,370,936 B1 * 4/2002 Yamagishi et al. ........... 73/1.35
6,553,818 B1 * 4/2003 Blumke et al. ........... 73/114.69

* cited by examiner

Primary Examiner—Hezron Williams
Assistant Examiner—Nathaniel Kolb
(74) Attorney, Agent, or Firm—Carlson, Gaskey & Olds

(57) ABSTRACT

A particulate sampler system includes a diluted exhaust mass flow controller that receives flow from a dilution mass flow controller and a laminar flow element (LFE). The dilution mass flow controller and LFE are fluidly arranged parallel to one another. A controller communicates with the mass flow controllers and the LFE to determine the flow through these devices, command valves in the mass flow controllers and generate data for determining calibration coefficients and correction factors. The diluted exhaust mass flow controller is calibrated and calibration coefficients are generated using a first to fourth order curve fit. Similarly, initial calibration coefficients are generated for the dilution mass flow controller. The diluted exhaust mass flow controller is set at a desired flow point. The dilution mass flow controller is varied between set points corresponding to different dilution ratios at the common, desired set point. The data obtained is used to determine a correction factor for example, by performing a linear curve fit of the data. The correction factor is applied to the calibration coefficients associated with the mass flow controllers.

17 Claims, 3 Drawing Sheets

… …

PARTICULATE SAMPLER SYSTEM FLOW CALIBRATION

This application corresponds to U.S. Provisional Application Ser. No. 60/664,277, filed Mar. 22, 2005.

BACKGROUND OF THE INVENTION

This invention relates to a method and apparatus for calibrating a particulate sampler system used in quantifying particulates from vehicle emissions.

Particulate sampler systems are used to quantify emission particulates from, for example, diesel engines for vehicles. The systems are used for engine development and to ensure compliance with governmental regulations concerning emissions of particulate matter.

The particulate sampler system must be calibrated to ensure its accuracy so that test results are reliable. The test procedures, calibration, and accuracies are often specified by various regulations and standards, such as ISO 16183. It is desirable to have better than five percent accuracy.

One typical particulate sampler system includes a probe that obtains a sample from an exhaust source. The sample is diluted using a diluent such nitrogen that flows through a dilution mass flow controller to mix with the exhaust sample in a dilution tunnel. The diluted sample flows through a diluted exhaust mass flow controller from which the diluted exhaust sample is then collected in a filter. The particulate matter from the exhaust source is calculated, in part, by determining the volume of sample collected. The mass flow through the dilution mass flow controller is subtracted from the mass flow of the diluted exhaust mass flow controller.

Prior to any testing, the mass flow controllers are calibrating using a laminar flow element (LFE), which is arranged in the particulate sampler system in place of the probe. Since the diluted exhaust mass flow controller is calibrated independently of the dilution mass flow controller, any calibration error in the diluted exhaust mass flow controller is transferred to the dilution mass flow controller during the calibration with the LPE. This results in what is referred to as a transfer error which can result in an accuracy that is worse than the desired five percent. What is needed is an improved calibration apparatus and procedure to improve the accuracy of the particulate sampler system.

SUMMARY OF THE INVENTION

The present invention includes a particulate sampler system having a diluted exhaust mass flow controller that receives flow from a dilution mass flow controller and a laminar flow element (LFE). The dilution mass flow controller and LFE are fluidly arranged parallel to one another. A controller communicates with the mass flow controllers and the LFE to determine the flow through these devices, command valves in the mass flow controllers and generate data for determining calibration coefficients and correction factors.

The diluted exhaust mass flow controller is calibrated and calibration coefficients are generated using a first to fourth order curve fit. Similarly, initial calibration coefficients are generated for the dilution mass flow controller. The diluted exhaust mass flow controller is set at a desired flow point. The dilution mass flow controller is varied between set points corresponding to different dilution ratios at the common, desired set point. The data obtained is used to determine a correction factor for example, by performing a linear curve fit of the data. The correction factor is applied to the calibration coefficients associated with the mass flow controllers. In this manner, the transfer error is addressed and the overall accuracy of the particulate sampler system is improved.

These and other features of the present invention can be best understood from the following specification and drawings, the following of which is a brief description.

DETAILED DESCRIPTION OF THE PREFERRED EMBODIMENT

Figure 1:
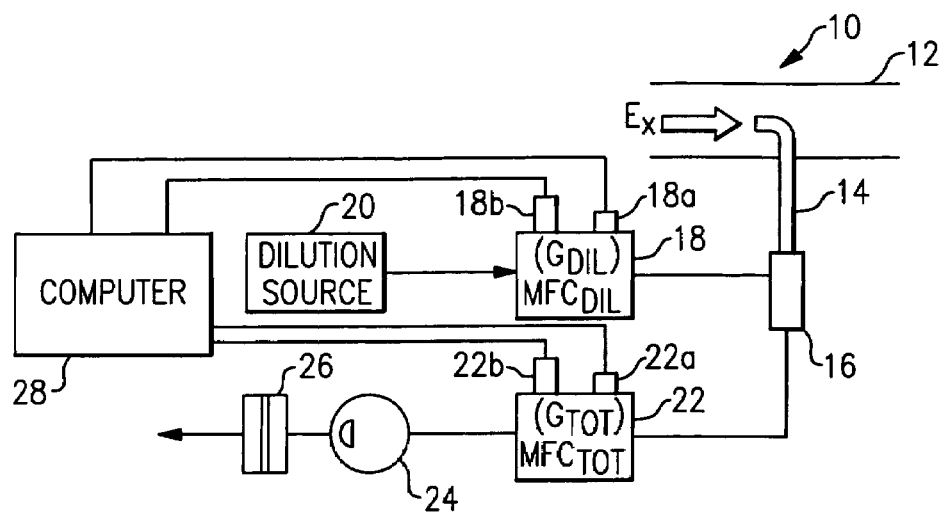
FIG. 1 is a schematic view of a particulate sampler system during a test procedure.

A schematic of a particulate sampler system 10 during a test procedure is shown in FIG. 1. The system 10 includes exhaust pipe 12 that carries exhaust from an emissions source such as a diesel engine in a vehicle. A probe 14 receives a portion of the exhaust for analysis. A diluent such as nitrogen flows from a dilution source 20 through a dilution mass flow controller 18 into a tunnel 16 where it mixes with the exhaust sample. The diluted exhaust sample flows through a diluted exhaust mass flow controller 22. A pump 24 draws the fluid through the system 10. The diluted exhaust sample flows through a filter 26 upon which particulates in the sample collect. The filter is later weighed to determine the mass of particulates within the sample. The total particulates are calculated, in part, by taking the difference of the mass flow measured by the diluted exhaust mass flow controller 22 and dilution mass flow controller 18 to determine the mass flow of the exhaust sample. Of course, the measurements of the mass flow controllers must be accurate in order to accurately determine the mass of the particulates in the exhaust sample.

The dilution and diluted exhaust mass flow controllers 18, 22 respectively include valves 18a, 22a and meters 18b, 22b. The valves 18a, 22a and meters 18b, 22b communicate with a computer 28, which controls the flow through the mass flow controllers and obtains data associated with the flow there through.

Figure 2:
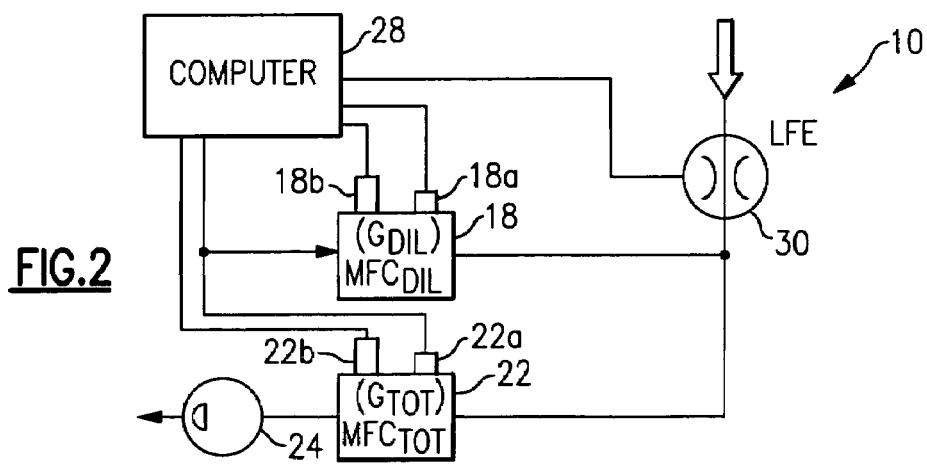
FIG. 2 is a schematic view of the particulate sampler system during a calibration.

The particulate sampler system 10 is shown in FIG. 2 undergoing a calibration. A laminar flow element (LFE) 30 is shown in place of the probe 14. The LFE 30 is a very accurate flow measurement device used to calibrate the mass flow controllers 18, 22. The computer 28 may communicate with the LFE 30 to determine the flow there through. It should be understood that the computer 28 can be one or more hardware and/or software devices.

Figure 3:
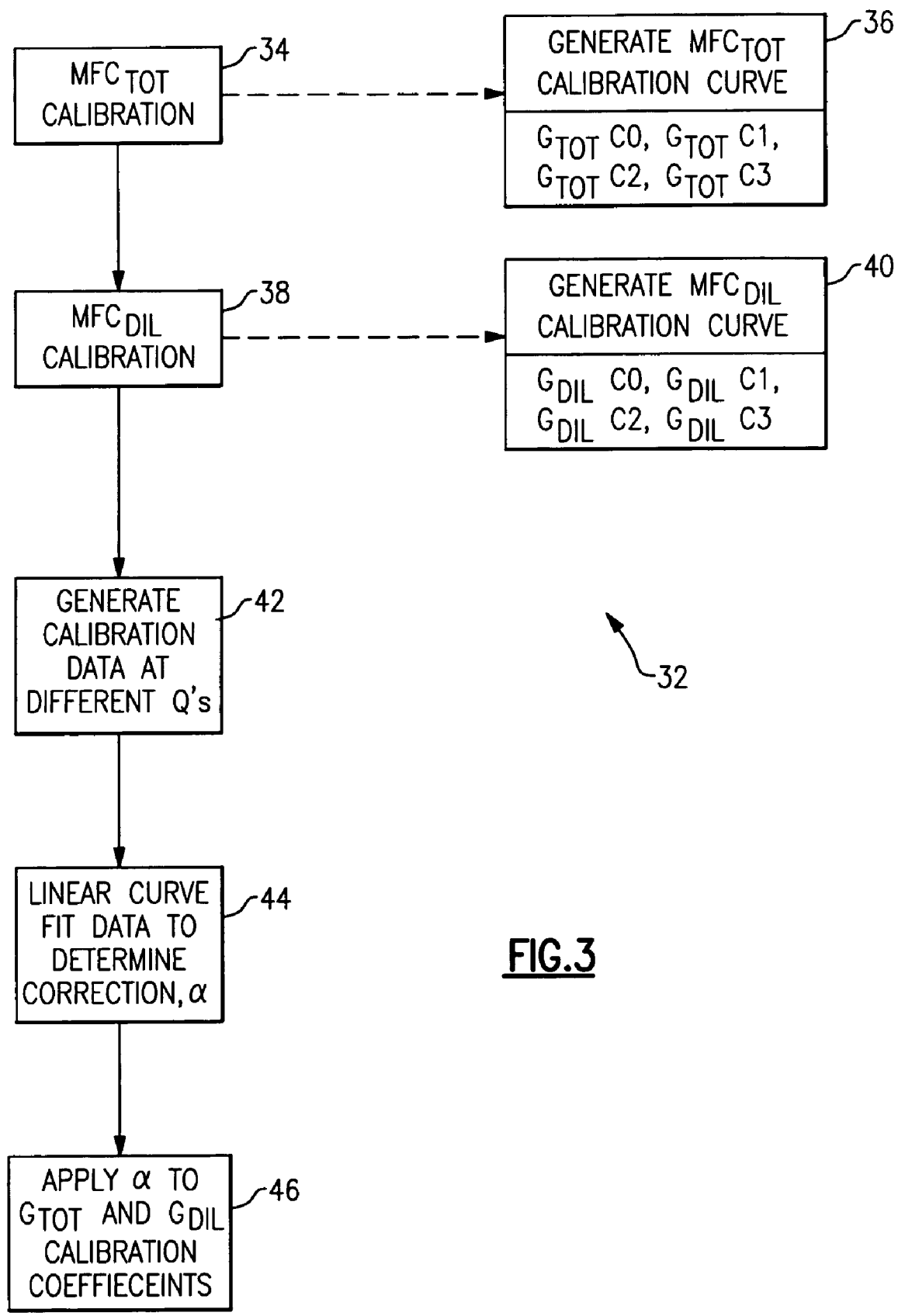
FIG. 3 is a flow diagram of a calibration procedure according to the present invention.

A calibration procedure 32 is illustrated in FIG. 3 and is highly schematic. The calibration procedure 32 may include more or fewer steps than shown. The diluted exhaust mass flow controller 22 is typically calibrated relative to another LFE (not shown in FIG. 2) to provide a calibrated diluted exhaust mass flow controller as indicated at block 34 in FIG. 3. The diluted exhaust mass flow calibration 34 generates coefficients for a calibration curve, shown at block 36, that is applied to all subsequent readings of the diluted exhaust mass flow controller 22 (C0-C3, as applied to diluted exhaust mass flow reading, $G_{TOT}$). Subtracting the flow measured by the dilution mass flow controller 18 from the flow measure by the diluted exhaust mass flow controller 22 should yield a flow that is equal to the flow measured by the LFE 30. Any difference in flows is compensated for at block 38. Calibration curve coefficients are generated for the dilution mass flow controller 18, as indicated at block 40 (C0-C3, as applied to dilution mass flow readings $G_{DIL}$). The above described calibrations are typical for a particulate sampler system. However, an undesirable, nonlinear transfer error may result which compromises the accuracy of the test results.

Table 1 below illustrates calibration data generated for a 70 millimeter filter diameter. The valves 18a, 22a are commanded by the computer 28 to the set points specified in Table 1. The non-bold, non-italic values illustrate the typical calibration data used to generate the calibration coefficients for the dilution mass flow controller 18. These values, which are a first set of calibration data, are kept at a constant flow differential (0.1 g/s in the example shown) to keep the LFE at a constant flow rate. In this manner, any error attributed to a variable flow rate in the LFE are avoided. The calibration curve coefficients for the dilution mass flow controller 18 are determined from this data by performing a polynomial curve fit.

TABLE 1

CALIBRATION DATA FOR A 70 mm FILTER DIAMETER

| $G_{TOT}$ Set Points (g/s) | $G_{DIL}$ Set Points (g/s) | Dilution ratio, Q |
|---|---|---|
| 0.8 | 0.7 | |
| ... | ... | |
| 1.1 | 1.0 | |
| *1.5* | *1.0* | *3* |
| 1.2 | 1.1 | |
| 1.3 | 1.2 | |
| *1.5* | *1.2* | *5* |
| 1.4 | 1.3 | |
| *1.5* | *1.35* | *10* |
| *1.5* | *1.4* | *15* |
| *1.5* | *1.45* | *30* |
| *1.5* | *1.47* | *50* |
| 1.6 | 1.5 | |
| ... | ... | |
| 2.2 | 2.1 | |

The inventive calibration, also obtains additional calibration data shown in bold italics in Table 1. For the example 70 millimeter filter diameter, a typical flow range during the test at the diluted exhaust mass flow controller 22 is from approximately 0.8 g/s-2.2 g/s. A set point of 1.5 g/s, which is approximately the midpoint of the flow range, is selected as a desired common flow set point. The valve 18a at the dilution flow controller 18 is varied to provide six different dilution ratios at the 1.5 g/s set point, as shown at block 42. This data, which are a second set of calibration data, is used to obtain a linear curve fit to determine a correction factor α, as shown in block 44. The data 50 and linear curve fit 48 is graphically illustrated in FIG. 4 according to mathematical relationships discussed below.

Equations 1-9 illustrate the mathematical calculations that may be used to determine the correction factor α. The equation for the dilution ratio, Q is illustrated by Equation 1.

$$Q = \frac{MFC_{TOT}}{MFC_{TOT} - MFC_{DIL}} \quad \text{(Equation 1)}$$

The flow through dilution mass flow controller can be represented by the equation illustrated in Equation 2.

$$MFC_{DIL} = MFC_{TOT}\left(1 - \frac{1}{Q}\right) \quad \text{(Equation 2)}$$

The difference between the diluted exhaust mass flow controller 22 and the dilution mass flow controller 18 should be equal to the flow through the LFE, as illustrated in Equation 3. The percent error if the result of Equation 3 is not equal to zero can be represented by Equation 4.

$$LFE = MFC_{TOT} - MFC_{DIL} \quad \text{(Equation 3)}$$

$$\%error = \frac{LFE - (MFC_{TOT} - MFC_{DIL})}{LFE} \quad \text{(Equation 4)}$$

The error attributable to each of the diluted exhaust mass flow controller and dilution mass flow controller are illustrated by Equations 5 and 6 respectively.

$$error(MFC_{TOT}) = \alpha MFC_{TOT} \quad \text{(Equation 5)}$$

$$error(MFC_{DIL}) = \alpha MFC_{TOT}\left(1 - \frac{1}{Q}\right) \quad \text{(Equation 6)}$$

By making the appropriate substitutions into Equation 4, the percent error can be expressed as shown in Equations 7 and 8.

$$\%error = \frac{LFE - \left(MFC_{TOT} + \alpha MFC_{TOT} - \alpha MFC_{TOT}\left(1 - \frac{1}{Q}\right)\right)}{LFE} \quad \text{(Equation 7)}$$

$$\%error = \frac{-\alpha MFC_{TOT}\frac{1}{Q}}{LFE} \quad \text{(Equation 8)}$$

Figure 4:
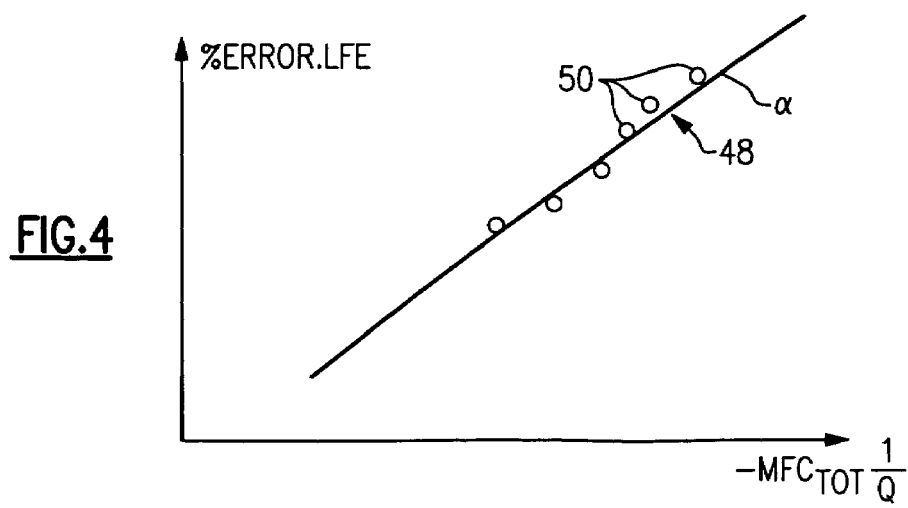
FIG. 4 is a graph of the data used to determine the correction factor using a linear curve fit.

The bold italic data from Table 1 is shown graphically in FIG. 4 according to the Equation 9.

$$\%error \cdot LFE = \alpha\left(-MFC_{TOT}\frac{1}{Q}\right) \quad \text{(Equation 9)}$$

A linear curve fit of the data points in FIG. 4 yields the correction factor α. The correction factor α can then be applied to each of the calibration coefficients (block 46 in FIG. 3) for the diluted exhaust mass flow controller 22 and dilution mass flow controller 18 as illustrated respectively in Equations 10 and 11.

$$MFC_{TOT}(\text{TRUE}) = MFC_{TOT}(\text{OLD}) + \alpha MFC_{TOT}(\text{OLD})$$

$$MFC_{TOT}(\text{TRUE}) = G_{TOT}C \cdot (1 + \alpha) \quad \text{(Equation 10)}$$

$$MFC_{DIL}(\text{TRUE}) = MFC_{DIL}(\text{OLD}) + \alpha MFC_{DIL}(\text{OLD})$$

$$MFC_{DIL}(\text{TRUE}) = G_{DIL}C \cdot (1 + \alpha) \quad \text{(Equation 11)}$$

In one example, α is limited to +/±0.04 to prevent the correction factor from adjusting the calibration coefficients more than desired. C represents a calibration coefficient, and the correction factor α is applied to each calibration coefficient (C0-C3) for each of the mass flow controllers 18, 22.

Figure 5:
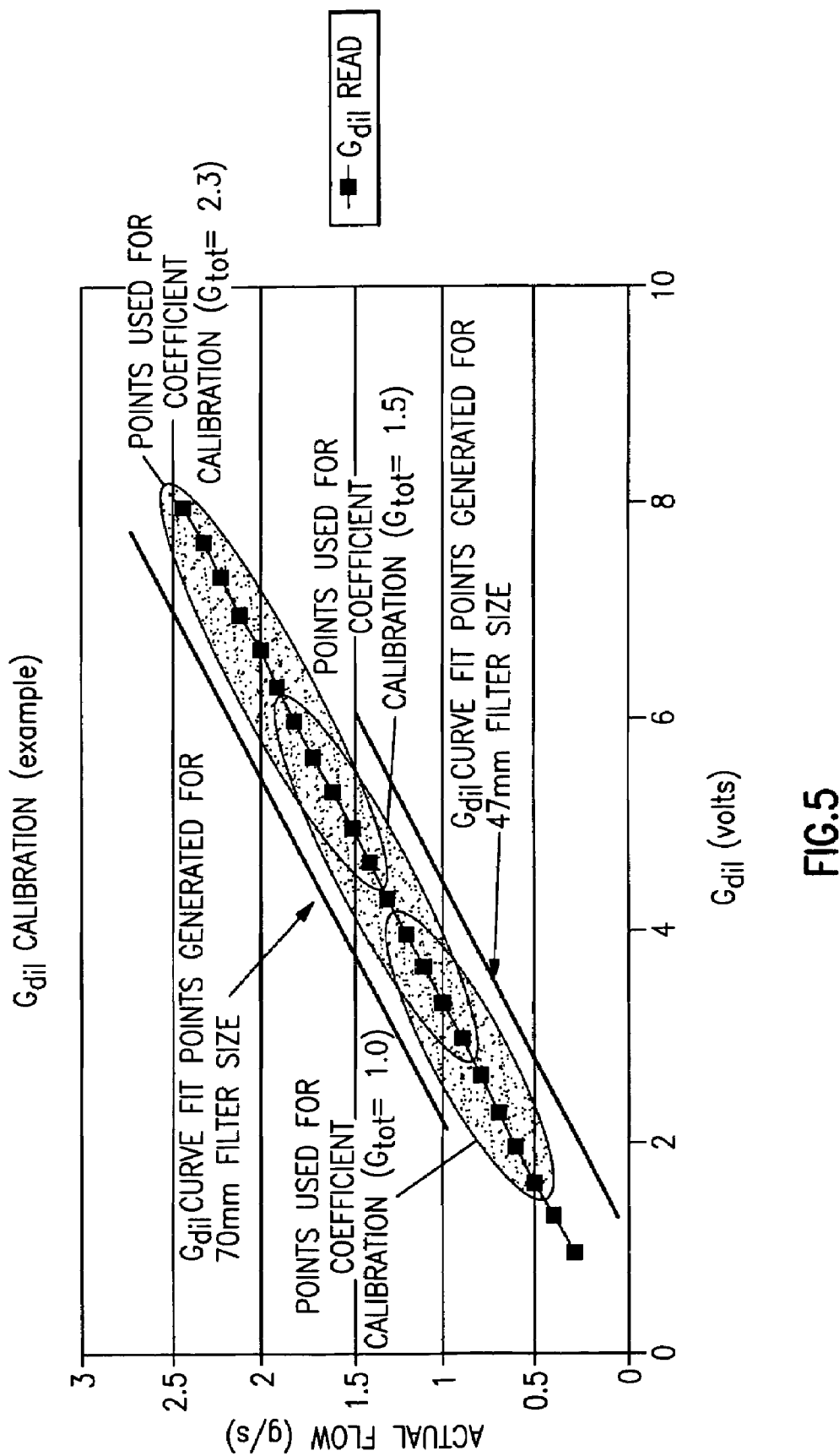
FIG. 5 is a graph illustrating data used to generate correction factors for different filter sizes according to the present invention.

FIG. 5 graphically illustrates the data generated for different filter sizes and different common set points within a flow range.

Although a preferred embodiment of this invention has been disclosed, a worker of ordinary skill in this art would recognize that certain modifications would come within the scope of this invention. For example, although the exemplary embodiment is a particulate sampler system, the inventive calibration is applicable to other types of flow measurement systems that use relative calibration between flow measurement devices. For these reasons, the following claims should be studied to determine the true scope and content of this invention.

What is claimed is:

1. A method of calibrating a flow measurement system comprising the steps of:
   a) generating calibration curves for first and second flow measurement devices;
   b) generating calibration data at a common flow point of one of the first and second flow measurement devices at different flow set points of the other of the first and second flow measurement devices to determine a correction factor; and
   c) applying the correction factor to at least one of the first and second flow measurement devices.

2. The method according to claim 1, wherein the first and second flow measurement devices are first and second mass flow controllers, and step a) is performed by comparing a difference in flow between the flow controllers to a flow through a laminar flow element.

3. The method according to claim 2, wherein the second mass flow controller and laminar flow element are arranged fluidly upstream from the first mass flow controller, the second mass flow controller and laminar flow element fluidly arranged parallel relative to one another.

4. The method according to claim 3, wherein step b) includes maintaining flow set points the common flow point at the first mass flow controller while the flow set points at the second mass flow controller are varied to obtain different dilution ratios.

5. The method according to claim 4, wherein the correction factor corresponds to a linear fit of calibration data associated with the common flow point.

6. The method according to claim 2, wherein step a) includes generating calibration coefficients for the mass flow controllers.

7. The method according to claim 6, wherein the correction factor is applied to the calibration coefficients of the first mass flow controller.

8. The method according to claim 6, wherein the correction factor is applied to the second mass flow controller.

9. The method according to claim 2, wherein step b) includes commanding flow set points in the first and second mass flow controllers separated by a constant flow rate differential while varied across the flow range.

10. The method according to claim 1, wherein step b) includes determining a flow range associated with a filter size and selecting the common flow point at a desired flow point at approximately a midpoint within the flow range.

11. A flow measurement system comprising:
   first, second and third flow measurement devices, the flow measurement devices fluidly arranged so that the first flow measurement device receives flows from the second and third flow measurement devices, which are fluidly arranged in parallel relative to one another; and
   a controller communicating with the flow measurement devices, the controller generating a first calibration curve for one of the first and second flow measurement devices when separated by a generally constant flow differential, and the controller obtaining data with one of the first and second flow measurement devices at a common flow point and the other of the first and second controllers at a varying flow to determine a second calibration curve corresponding to a correction factor, and applying the correction factor to the first calibration curve to generate a third calibration curve.

12. The flow measurement system according to claim 11, wherein the first and second flow measurement devices are first and second mass flow controllers and the third flow measurement device is a laminar flow element.

13. The flow measurement system according to claim 11, wherein the mass flow controllers include valves that are commanded to flow set points by the controller during a calibration procedure, the flow set points associated with one mass flow controller separated by a constant flow rate as compared to the flow set points of the other mass flow controller during a first calibration to obtain the first calibration curve.

14. The flow measurement system according to claim 13, wherein the valve of the first mass flow controller is maintained at a common flow point while the valve of the second mass flow controller is varied to obtain different dilution ratios, which corresponds to the second calibration curve.

15. The flow measurement system according to claim 14, wherein the second calibration curve is a linear curve fit corresponding to a correction factor.

16. The flow measurement system according to claim 15, wherein the correction factor is applied to calibration coefficients for the first and second mass flow controllers, which correspond to the first calibration curve, to obtain new calibration coefficients corresponding to the third calibration curve.

17. The flow measurement according to claim 11, wherein the common flow point falls within a flow range corresponding to a filter size.

* * * * *

UNITED STATES PATENT AND TRADEMARK OFFICE
CERTIFICATE OF CORRECTION

PATENT NO.        : 7,607,335 B2
APPLICATION NO.   : 11/386911
DATED             : October 27, 2009
INVENTOR(S)       : Marek et al.

It is certified that error appears in the above-identified patent and that said Letters Patent is hereby corrected as shown below:

IN THE CLAIMS:

Claim 11, column 6, line 22: "controllers" should be replaced with --flow measurement devices--

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,607,335 B2
APPLICATION NO. : 11/386911
DATED : October 27, 2009
INVENTOR(S) : Marek et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 889 days.

Signed and Sealed this

Twelfth Day of October, 2010

David J. Kappos
*Director of the United States Patent and Trademark Office*